(12) United States Patent
Ganzoni et al.

(10) Patent No.: US 7,400,938 B2
(45) Date of Patent: Jul. 15, 2008

(54) METHOD FOR ASSIGNING STATES TO STITCHES OF A FABRIC

(75) Inventors: Stefan Ganzoni, Bottmingen (CH); Alain Berthéas, Saint-Just Saint-Rambert (FR); Christophe Fayolle, Precieux (FR); Robert Austernaud, St. Chamond (FR); Hervé Scelles, Saint-Just Saint-Rambert (FR); Florence Mathieu, St. Galmier (FR)

(73) Assignee: Ganzoni Management AG (NL)

( * ) Notice: Subject to any disclaimer, the term of this patent is extended or adjusted under 35 U.S.C. 154(b) by 0 days.

(21) Appl. No.: 11/774,410

(22) Filed: Jul. 6, 2007

(65) Prior Publication Data

US 2008/0047305 A1 Feb. 28, 2008

(30) Foreign Application Priority Data

Jul. 12, 2006 (EP) .................................. 06014480

(51) Int. Cl.
*G06F 19/00* (2006.01)

(52) U.S. Cl. ........................................ 700/132; 66/232

(58) Field of Classification Search .................. 66/231, 66/232, 237; 700/131, 132
See application file for complete search history.

(56) References Cited

U.S. PATENT DOCUMENTS

| 3,844,139 | A | * | 10/1974 | De Cerjat et al. | ............. 66/215 |
| 4,332,150 | A | | 6/1982 | Grözinger | ..................... 66/232 |
| 5,758,697 | A | * | 6/1998 | Musha et al. | ................ 139/192 |
| 6,321,574 | B1 | * | 11/2001 | Marker et al. | ................... 66/19 |

* cited by examiner

*Primary Examiner*—Danny Worrell
(74) *Attorney, Agent, or Firm*—Ostrolenk, Faber, Gerb & Soffen, LLP

(57) ABSTRACT

The present invention relates to a method for assigning states to stitches of a fabric, wherein the state can vary between a first and a second state, that comprising the steps of allocating a part of the fabric, randomly assigning a state to each stitch of the allocated part of the fabric, evaluating the ratio between the number of stitches in the first state and the number of stitches in the second state, checking if the ratio lies within a predefined range of values, and restarting at step b) if the ratio lies outside the predefined range. The method may be used for manufacturing a medical compression garment.

16 Claims, 12 Drawing Sheets

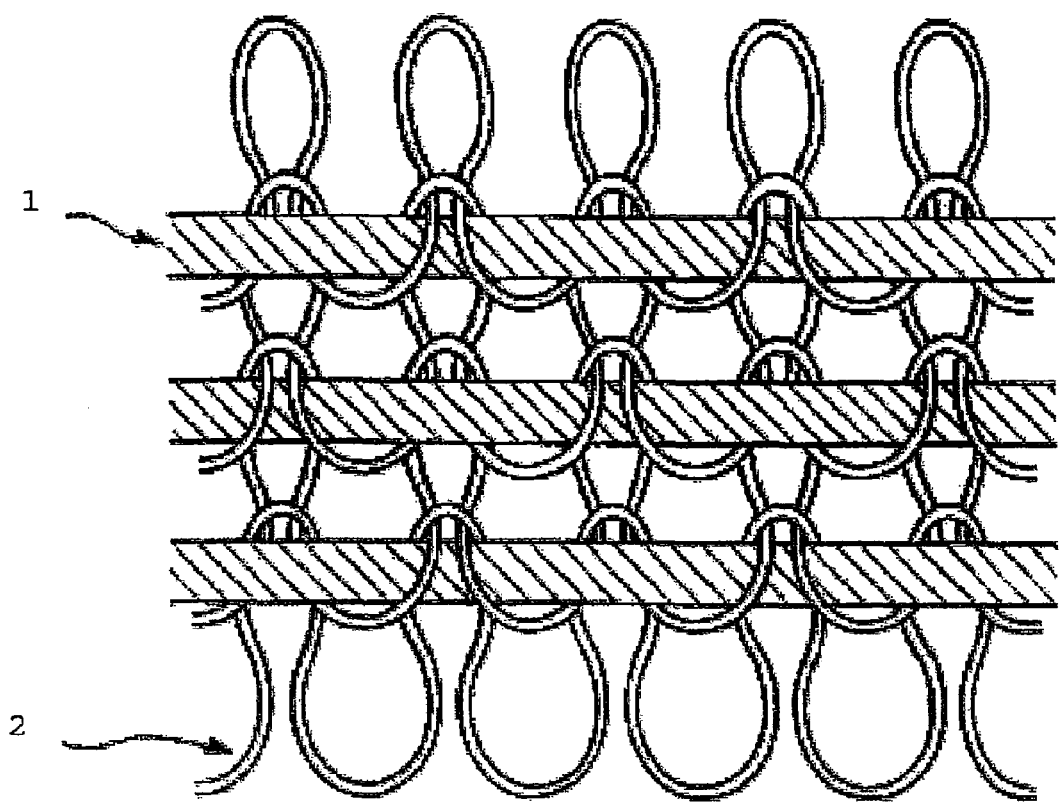
Fig. 1 - PRIOR ART -
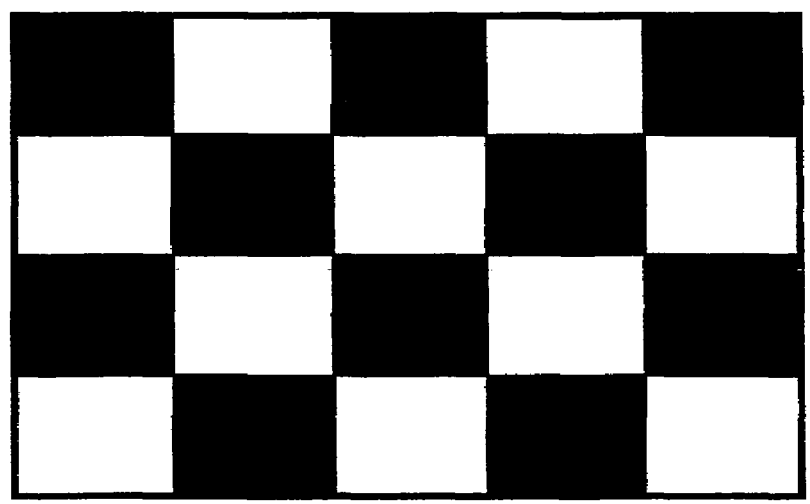
Fig. 2 - PRIOR ART -

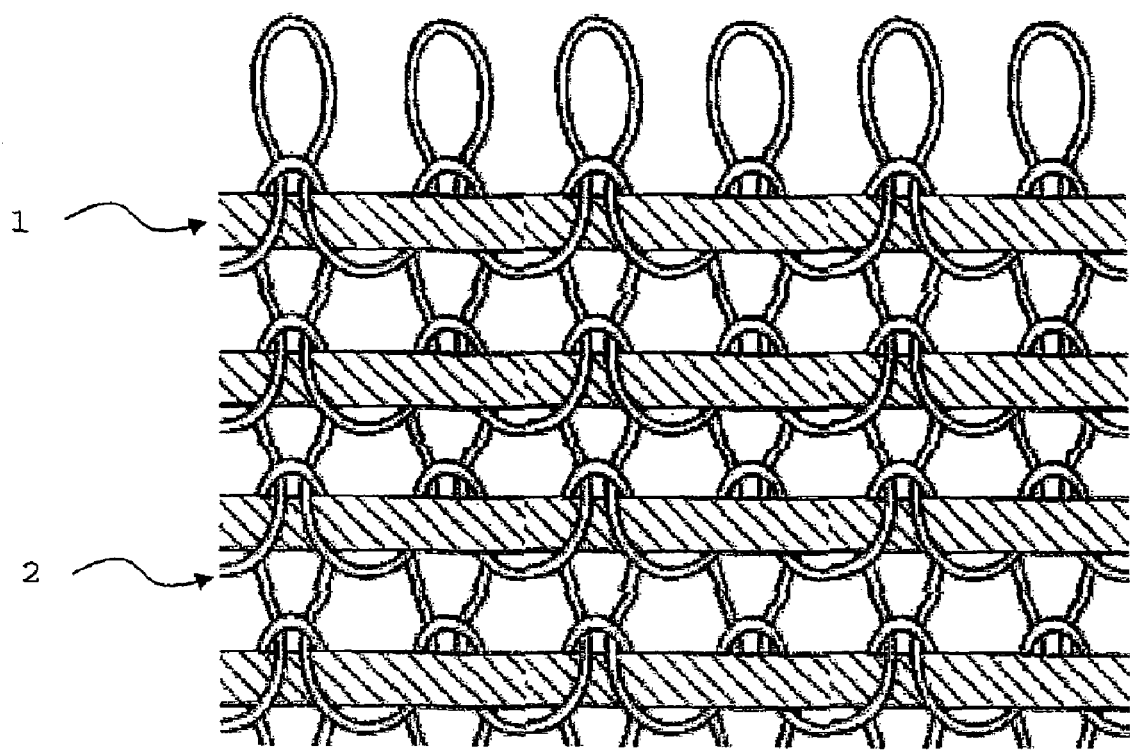
Fig. 3 — PRIOR ART —
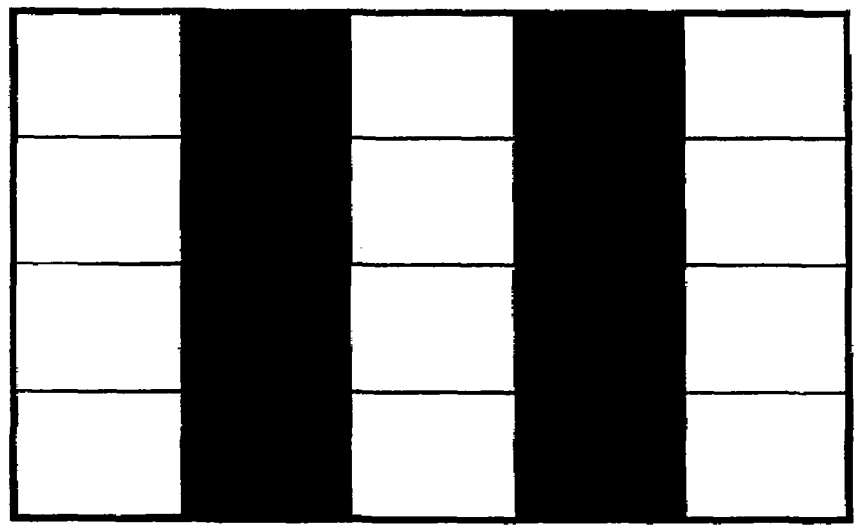
Fig. 4 — PRIOR ART —

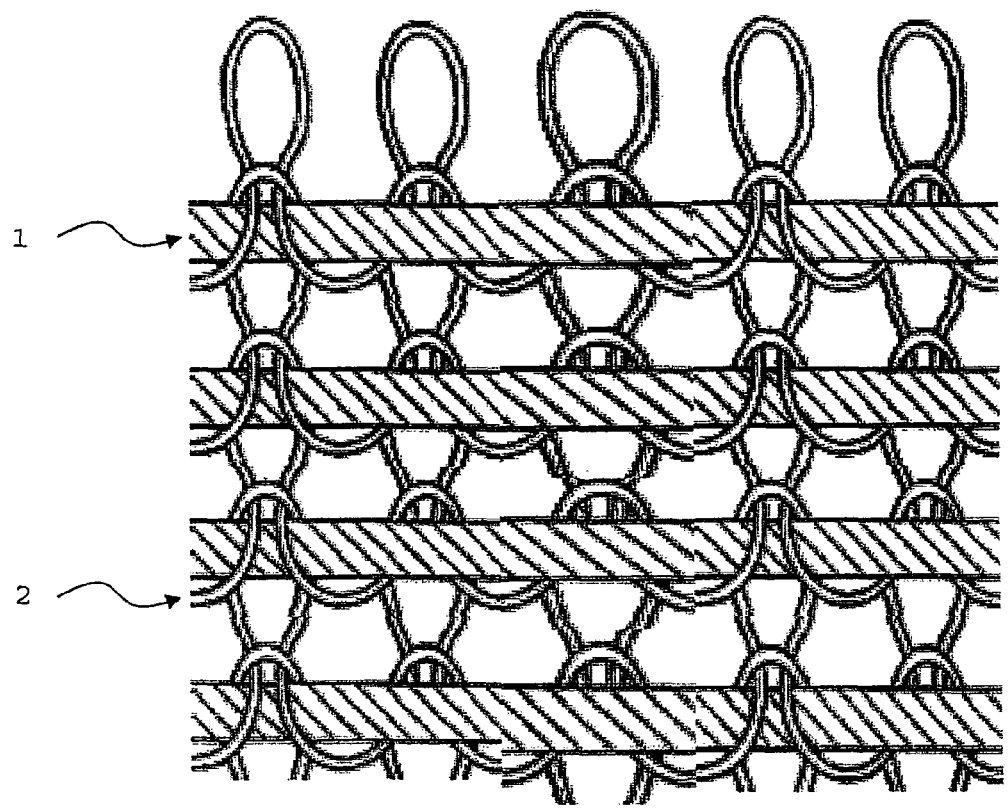
Fig. 5 — PRIOR ART —
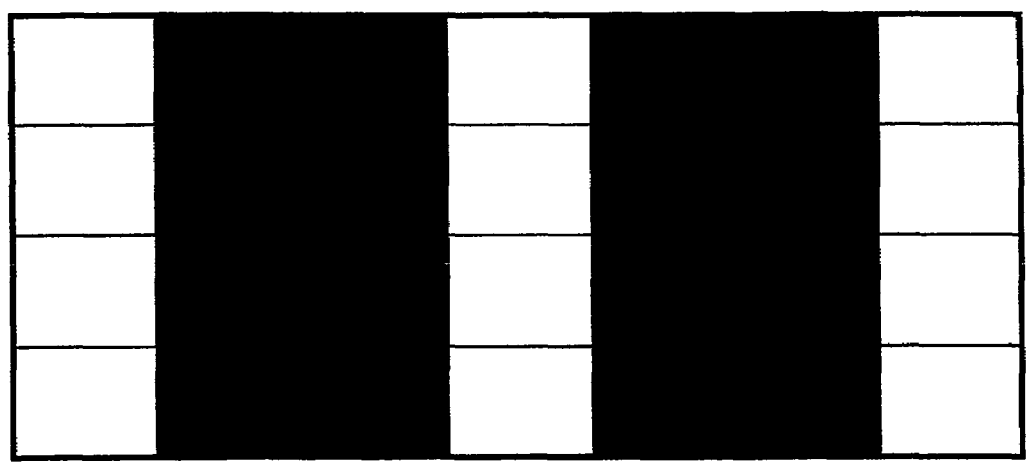
Fig. 6 — PRIOR ART —

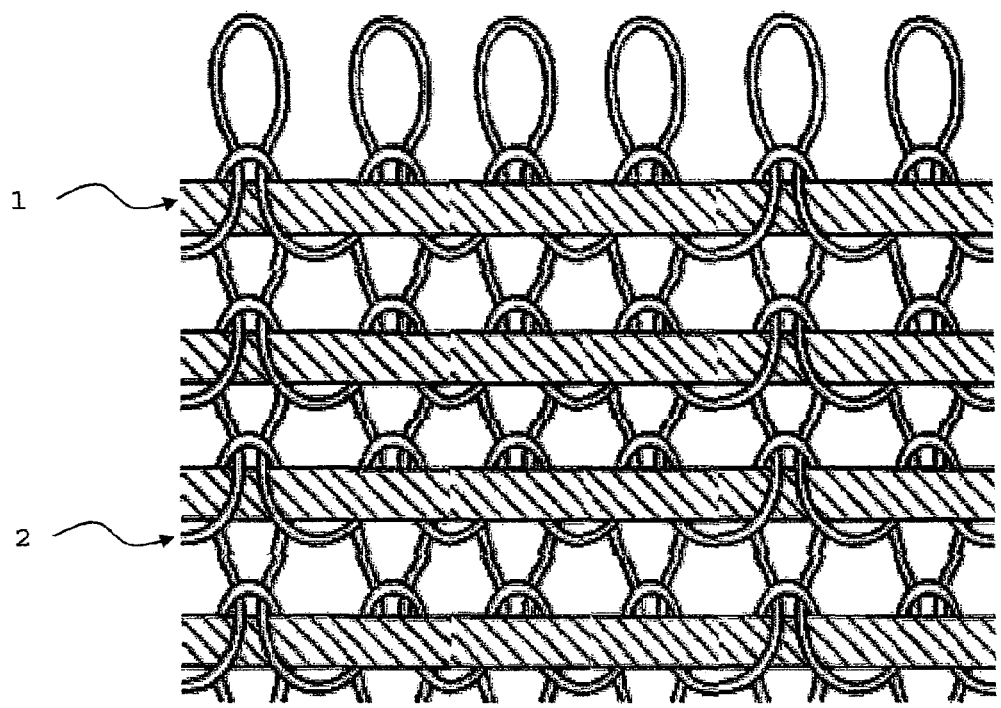
Fig. 7    - PRIOR ART -
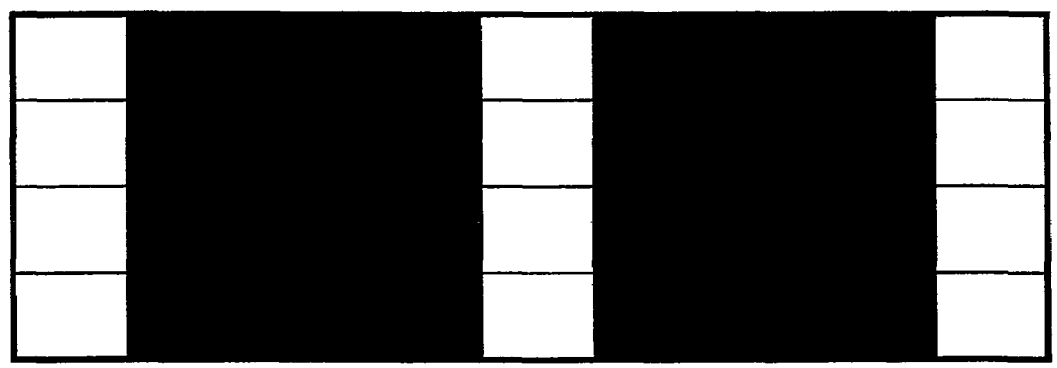
Fig. 8    - PRIOR ART -

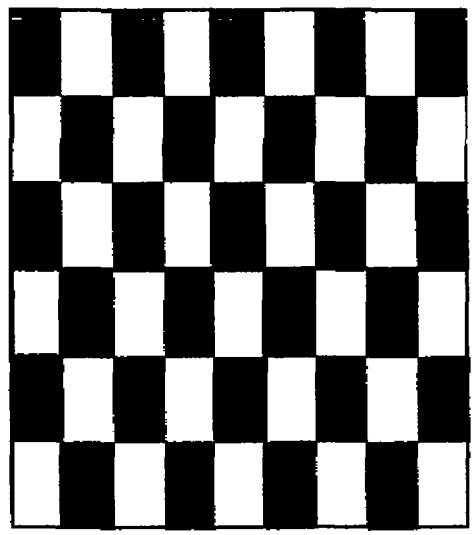
Fig. 9    - PRIOR ART -
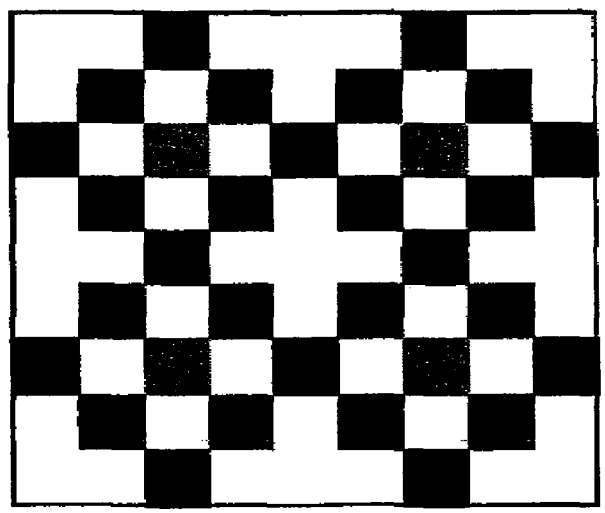
Fig. 10    - PRIOR ART -

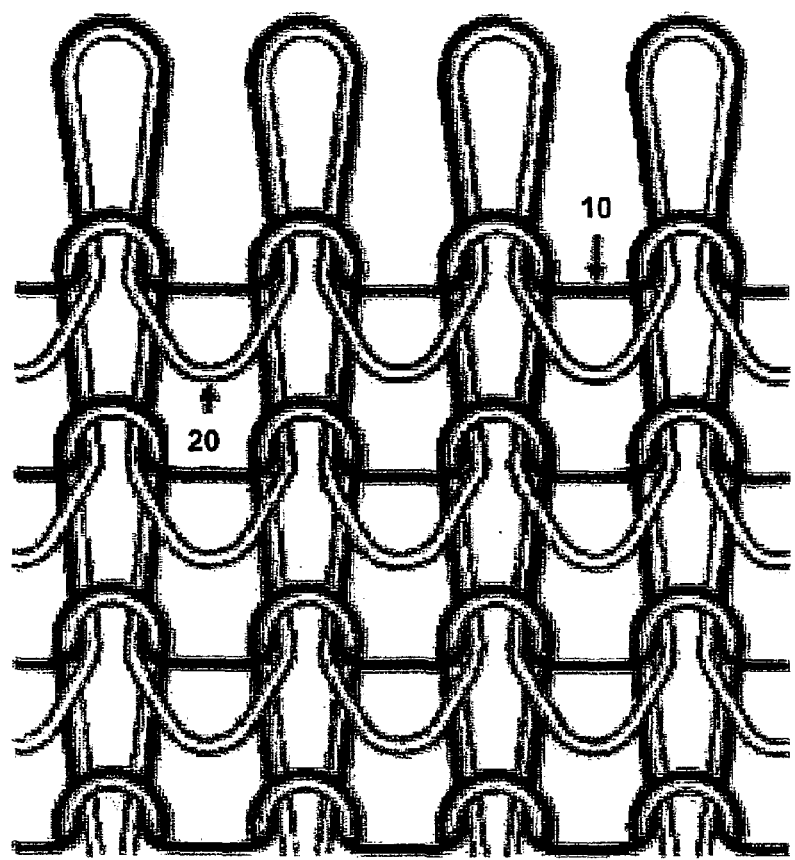
Fig. 11 - PRIOR ART -
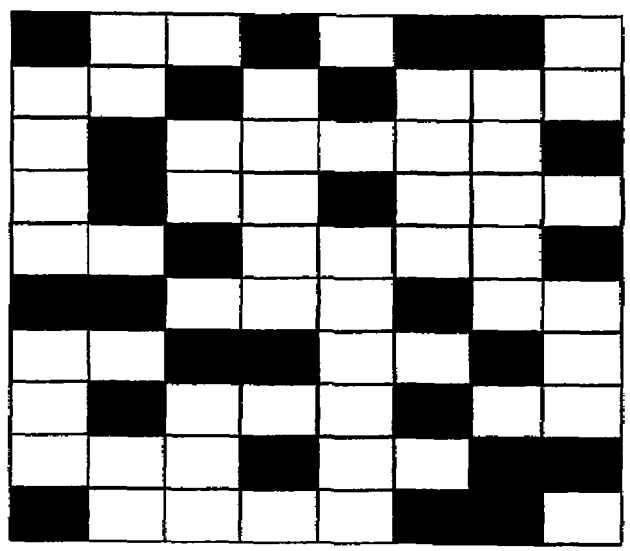
Fig. 12

METHOD FOR ASSIGNING STATES TO STITCHES OF A FABRIC

CROSS REFERENCE TO RELATED APPLICATION

The present application claims priority of European Patent Application No. 06 014 480.5, filed Jul. 12, 2006, the disclosure of which has been incorporated herein by reference.

TECHNICAL FIELD

The present invention relates to a method for allocating a state of a stitch of a fabric and the use of such a method for manufacturing medical compression garments with a certain knitting pattern.

BACKGROUND OF THE INVENTION

Medical compression garments (abbreviated by MCG) are garments which are mainly made of elastic knitted fabric. Their aim is to provide a pressure or compressive force, respectively, to a human skin, especially to a limp such as an arm or a leg, for e.g. the treatment of venous diseases and lymphatic disorders. The patients are usually required to apply some form of orthese during an entire day for a long period of their lifetime and therefore it is desirable to provide an orthese in form of a garment. Patients are generally more compliant with wearing the medical compression garment if it is comfortable to wear. Medical compression garments can for example be used to compress a leg below the knee, an entire leg, an arm, a hand and so on. They can be designed in the form of stockings, socks, panties, sleeves, gloves, etc.

Medical compression garments are usually classified by size and compression strength and must comply with normative specifications in some countries such as the German norm RAL-GZ 387 or the French norms NF G 30-102b. These norms impose technical requirements for ensuring the medical effect of a medical compression garment. Criteria to be checked are the used materials and the physical performance of the medical compression garment. The requirements imposed on the manufacture of the fabric, of which the medical compression garment consists, concern the combination of so called inlaid yarns with so called loop yarns. Today the type of knitting machines which can be used to manufacture medical compression garments that fulfil the norm requirements is limited.

Depending on the knitting pattern different appearances and functional effects can be obtained. The functional effect determines if a patient complies with the necessity to wear an orthese in form of a medical compression garment. FIGS. 1 to 10 show examples of known knitting patterns or stitch patterns, respectively, for fabrics which are used for medical compression garments. The displayed stitch patterns can be produced with available types of knitting machines.

FIGS. 1 and 2 show the so called plain stitch pattern. Two yarns 1 and 2 are used, one yarn being the so called inlaid yarn and the other yarn being the so called loop yarn 2. At the crossing point of an inlaid yarn 1 and a loop yarn 2 there are two possibilities of yarn combinations that determine the state of the particular stitch defined by the crossing point. When the loop yarn 2 is in front of the inlaid yarn 1 (referring to the fabrics outside, i.e. the side/surface opposite to the side/surface looked at in the figures), then the stitch defined by the crossing point has the state "on". When the loop yarn 2 is located behind the inlaid yarn 1, then the stitch has the state "off". A pattern in which the states of horizontally and vertically consecutive stitches are assigned the states "on" or "off" is called stitch pattern. FIG. 2 shows a diagram of a plain stitch pattern wherein each stitch that has the state "on" is represented by a black rectangle and each stitch that has the state "off" is represented by a white rectangle.

FIG. 3 displays the known rib 1/1 stitch pattern. FIG. 4 shows the corresponding diagram with stitches having the state "on" as black rectangles and stitches having the state "off" as white rectangles. A fabric with the rib 1/1 pattern consists of alternating columns of stitches having either the state "on" or the state "off".

FIG. 5 shows the known rib 1/2 stitch pattern and FIG. 6 shows the respective diagram with rectangles whose colour depends on the state of the corresponding stitch. The rib 1/2 stitch pattern is characterised by a column of stitches having the state "off" that is followed by two columns of stitches having the state "on" which are in turn followed by a column of stitches having the state "off".

FIG. 7 shows the known rib 1/3 stitch pattern and FIG. 8 shows the corresponding diagram. Inbetween two parts of a fabric each consisting of three columns of stitches in the state "on" there is one column of stitches having the state "off".

FIGS. 9 and 10 show further examples of stitch patterns known in the state of the art. Theoretically, there are endless possibilities of stitch patterns providing certain visual effects, e.g. the Jacquard knitting, however the number of stitch patterns complying with the normative requirements is limited.

One of the important aspects for the provision of wear comfort is the thickness of the fabric. By employing the so called terry-loop pattern a bulky fabric with a certain thickness can be obtained which is comfortable to wear. The terry-loop pattern can, however, not be manufactured with the knitting machines which are currently used for manufacturing medical compression garments. These knitting machines have usually 20 to 32 needles per inch (787 to 1260 needles per meter) and a diameter of 3¾ to 6⅕ inch (95.25 millimetres to 157.48 millimetres). FIG. 11 displays a fabric with the terry-loop pattern. The bulky aspect of the terry-loop pattern is obtained by the so called terry yarn 20 which sticks out of the fabric by some extra length and is not held or retained by the ground yarn 10.

The known stitch patterns of medical compression garments displayed in FIGS. 1 to 10 may have bulky parts in the fabric when the loop yarn 2 is located in front of the inlaid yarn 1. Hence, a certain fabric thickness can be achieved if a stitch has the state "on". As far as the plain stitch pattern shown in FIGS. 1 and 2 is concerned, the bulky aspect is, however, rather limited. The bulky aspect is increased when there are more than two horizontally consecutive stitches having the state "on". This is the case for the stitch patterns displayed in FIGS. 5 to 8, wherein the rib 1/3 pattern has more bulky parts than the rib 1/2 pattern.

The rib patterns all lead to fabrics with ribs or parts form similar to a rib. Not all patients may want to wear medical compression garments consisting of fabrics with ribs. Furthermore, the provision of ribs, especially the provision of relatively wide ribs as being the case for the rib 1/3 pattern, may lead to structural instabilities of the fabric or the medical compression garment, respectively.

Patent document U.S. Pat. No. 4,332,150 discloses a fabric-producing machine in combination with a patterning system which implements a non-repeating pattern, wherein the patterning system comprises means for generating pattern-control signals randomly and pattern-limiting means that are operative for automatically imposing predetermined patterning restraints upon the pattern-control signals and for limiting the number of immediately consecutive joining identical stitches formed in a course. The produced fabric comprises courses and wales.

SUMMARY OF THE INVENTION

An object of the present invention is to provide a method for assigning states to stitches of a fabric for medical compression garments which leads to a medical compression garment with high wear comfort which preferably can be manufactured by using already existing knitting machines for manufacturing medical compression garments. Norm requirements on the fabric shall preferably be met.

It is a further object of the invention to provide a method for assigning states to stitches of a fabric by which a fabric can be manufactured that has bulky parts, preferably by using existing knitting machines and yarns which are usually employed when manufacturing medical compression garments. Preferentially, the bulky parts of the fabric shall have a similar touch as a fabric with a terry-loop stitch pattern.

It is a still further object of the invention to provide a method for assigning states to stitches of a fabric by which a fabric with bulky parts can be produced that does not comprise consecutive ribs.

In order to implement these and still further objects of the invention, which will become more readily apparent as the description proceeds, a method for assigning states to stitches of a fabric is provided, wherein a state can vary between a first and a second state said method comprising the following steps:

a) allocating a part of the fabric, b) randomly assigning a state to a stitch of said part of the fabric, c) evaluating the ratio between the number of stitches in the first state and the number of stitches in the second state, d) checking if the ratio lies within a predefined range of values, and e) restarting at a step b) if the ratio lies outside of the predefined range. If according to the result of step d) of the method the ratio between the number of stitches in the first state and the number of stages in the second state lies within the predefined range of values then a valid state has been assigned to each stitch of the allocated part of the fabric. Preferably, the least value of the predefined range is 0.2 and the greatest value of the predefined range is 0.8. The stitch pattern is formed in a random way, by randomly assigning either a first state or a second state to each of the horizontally or vertically consecutive stitches.

An inlaid yarn and a loop yarn are used to form the stitch pattern and the loop yarn is positioned in front of the inlaid yarn in the first state of a stitch and the loop yarn is positioned behind the inlaid yarn in a second state of the stitch. Hence, the first state of a stitch corresponds to the state "on" and the second of the stitch corresponds to the state "off" as described above. By assigning the first of the second state randomly to a stitch, a fabric can be obtained which com-prises no ribs. The optical and physical rib effect can be eliminated by the randomisation and the fabric appears to have a fuzzy nature, at least when viewed from a certain distance. The method can be applied for manufacturing a compression garment or the compressive part of a medical compression garment.

Existing knitting machines for manufacturing medical compression garments can be used and normative requirements can be met. Hence, the method can be implemented on knitting machines with 16 to 32 needles per inch (630 to 1260 needles per meter).

By ensuring that the ratio between the number of stitches in the first state and the number of stitches in the second state lies within the pre-defined range, preferably 0.2 and 0.8, long material durability can be achieved and the creation of areas with a critical material weakness can be avoided. Such areas of critical material weakness might for example appear if many stitches having the same state are grouped together. Because of the randomness of the state assignment such functional inconveniences can be avoided.

Furthermore, the appearance of a fabric and a medical compression garment made of the fabric can be improved as the number of consecutive stitches having the same state can be reduced.

The method may further include the steps of evaluating the number of stitches in the first state and the number of stitches in the second state for each row of the allocated part of the fabric, checking if the number of stitches in the same state lies between 2 and 6, preferably between 3 and 5, and restarting at step b) if the number of stitches in the same state is greater than 6 or smaller than 2, preferably greater than 5 or smaller than 3. Also, the method may provide the steps of evaluating the number of stitches in the first state and the number of stitches in the second state for each column of the allocated part of the fabric, checking if the number of stitches in the same state lies between 2 and 20, preferable between 2 and 10, and restarting at step b) if the number of stitches in the same state is greater than 20 or smaller than 2, preferably greater than 10 or smaller than 2.

These additional steps lead to a further improvement of the appearance and the functionality of a fabric or a medical compression garment, respectively, manufactured by employing the method. Large groups of stitches having the same state can be avoided and durability is further improved. By checking the stitches of each row and of each column, that is, by checking the stitches in the horizontal and in the vertical direction double control is applied.

Also, wear comfort is improved as the fabric or the medical compression garment, respectively, formed by employing the method contains parts with a certain thickness. Hence, the fabric and the medical compression garment feel comfortable on the skin and are pleasant to touch.

The method can be interpreted as an application of the so called fuzzy logic. The deviation of the ratio between the number of stitches in the first state and the number of stitches in the second state from an optimal ratio is evaluated and compared with a set of allowable deviations that span a certain predefined range. Furthermore, ranges are predefined, in which the number of stitches in the same state of each row, and the number of stitches of the same state of each column have to lie. The predefined ranges are required for controlling the stitch pattern and, hence, the appearance and the functionality of a fabric or a medical compression garment manufactured by employing the method.

After a valid state has been assigned to each stitch of the first allocated part of the fabric, a further part of the fabric may be allocated and the method steps may be performed on that further part of the fabric. Of course, instead of using the method of the invention for the further part, a different method may be used to produce a different type of pattern, e.g. the rib 1/3 stitch pattern or the plain stitch pattern (confer FIG. 18). Hence, the method may be performed for the entire fabric of a medical compression garment or only for a part of it, for example the sole area or/and the instep of the medical compression garment while the remaining fabric part has another stitch pattern, e.g. the plain stitch pattern.

For performing the method, the inlaid yarn preferably comprises elastic material (for example so called spandex), especially with a yarn count of 200 dtex to 1500 dtex. "Dtex" is one unit of measure for the yarn count. It is defined as the mass in grams per 10000 meters. The inlaid yarn may be covered by a first covering yarn, especially with a first covering yarn having a yarn count of 22 dtex to 400 dtex. The covering may be single or double.

The employed loop yarn preferably comprises elastic material and especially has a yarn count of 11 dtex to 78 dtex. It may be an intermingled yarn, which has been manufactured e.g. by so called air-chat processing, resulting from a combination of staple fibres and/or multi-filaments and elastic yarns. A second covering yarn may be used, especially a second covering yarn having a yarn count of 22 dtex to 200 dtex. The covering may be single or double. The loop yarn can comprise synthetic, artificial and/or natural fibres.

The inlaid yarn may be dyed in a different shade of colour than the loop yarn and/or the second covering yarn. Similarly, the first covering yarn may be dyed in a different shade of colour than the loop yarn and/or the second covering yarn. The different shades can be achieved by balancing the percentage of each dye used. By using different shades for the different types of yarns or fibres (natural/synthetic) used the visual appearance or the fuzzy effect, respectively, achieved when applying the method is emphasised. The appearance of the fabric or the medical compression garment manufactured when applying the method is approved.

BRIEF DESCRIPTION OF THE DRAWINGS

Further advantageous features and applications of the invention can be found in the dependent claims as well as in the following description of the drawings illustrating the invention. In the drawings like reference signs designate the same or similar parts throughout the several figures of which:

FIG. 1 shows a plain stitch pattern,
FIG. 2 is a diagram that illustrates the states of the stitches of a plain stitch pattern,
FIG. 3 shows a rib 1/1 stitch pattern,
FIG. 4 is a diagram illustrating the states of the stitches of the rib 1/1 stitch pattern,
FIG. 5 shows a rib 1/2 stitch pattern,
FIG. 6 is a diagram illustrating the states of the stitches of the rib 1/2 stitch pattern,
FIG. 7 shows a rib 1/3 stitch pattern,
FIG. 8 is a diagram illustrating the states of the stitches of the rib 1/3 stitch pattern,
FIG. 9 is a diagram illustrating the states of the stitches of a further stitch pattern which can be generated by existing knitting machines,
FIG. 10 is a diagram illustrating the states of the stitches of a still further stitch pattern which can be generated by a existing knitting machines,
FIG. 11 shows the terry-loop stitch,
FIG. 12 is a diagram illustrating the states of the stitches of a stitch pattern generated by the method according to the invention.

DESCRIPTION OF PREFERRED
EMBODIMENTS OF THE INVENTION

FIGS. 1 to 11 have been described in the introductory part of the description. It is referred thereto.

FIG. 12 shows stitches of a stitch pattern generated by the method according to the invention. The stitches can assume two different states. Referring to the fabrics exterior, in a first state the loop yarn is positioned in front of the inlaid yarn (so called "on"-state) and in a second state the loop yarn is positioned behind the stitch yarn (so called "off"-state). The state "on" is illustrated by a black rectangle and the state "off" is illustrated by a white rectangle. As can be seen from FIG. 12, stitches with different states appear to be randomly distributed. In this way a fabric having a fuzzy appearance can be manufactured while maintaining fabric durability.

Figure 13:
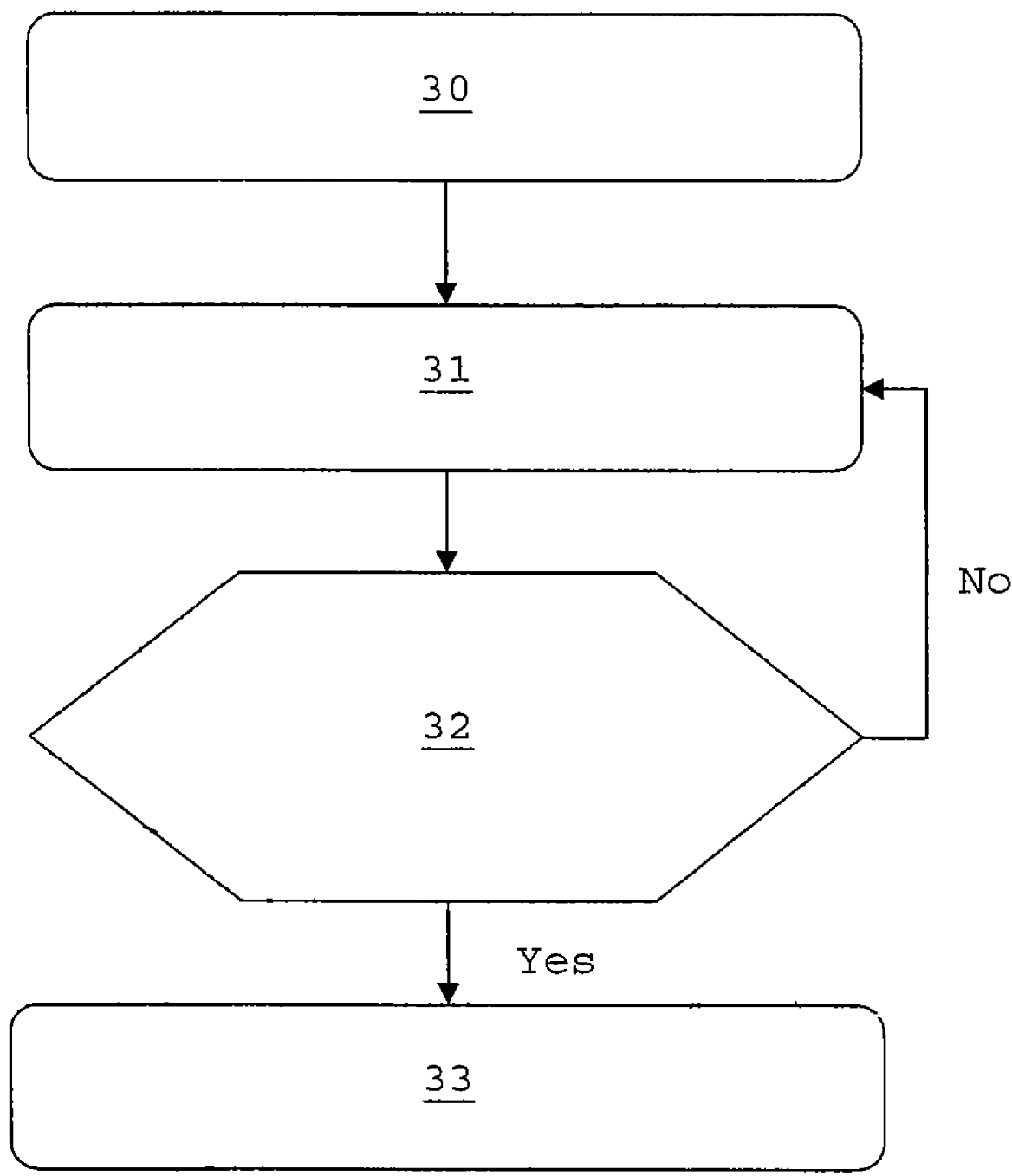
FIG. 13 is a flow chart of a preferred embodiment of the method according to the invention.

FIG. 13 shows a flow chart of a preferred embodiment of the method according to the invention. The method shall be applied to a given fabric defined by a given number of rows and a given number of columns and a given number of stitches per row and per column. The optimal ratio $\lambda$ between the stitches having the state "on" and the stitches having the state "off" is assigned a certain value that depends on the machine gauge and the size of the yarns to be used.

In a first step 30 a part of the fabric is allocated onto which the method shall be applied. In a second step 31 one of the states "on" and "off" is randomly assigned to each stitch of the allocated part of the fabric. Any known randomization algorithm can be used for the assignment. In a third step 32 the number of stitches having the state "on" and the number of stitches having the state "off" is evaluated or determined, respectively. Then, it is checked if the current ratio between the number of stitches having the state "on" and the number of stitches having the state "off" is the same as the optimal ratio $\lambda$ and if not, how much the current ratio differs from the optimal ratio $\lambda$. That is, the membership degree of the current ratio when compared to the optimal ratio $\lambda$ is evaluated. It is evaluated how much the current ratio "is a member of" the optimal ratio $\lambda$.

If the current ratio is far from the optimal ratio $\lambda$ (pure membership degree) then the method starts again at the second step 31 by randomly assigning a state to each stitch. If the current ratio is close enough to the optimal ratio $\lambda$, preferably has a value between 0.2 and 0.8, meaning that 20 to 80% of the loop yarns are positioned in front of the inlaid yarns, i.e. 20 to 80% of the stitches having the "on"-state, then a valid set of states has been assigned to the stitches and the method may end in step 33.

Figure 14:
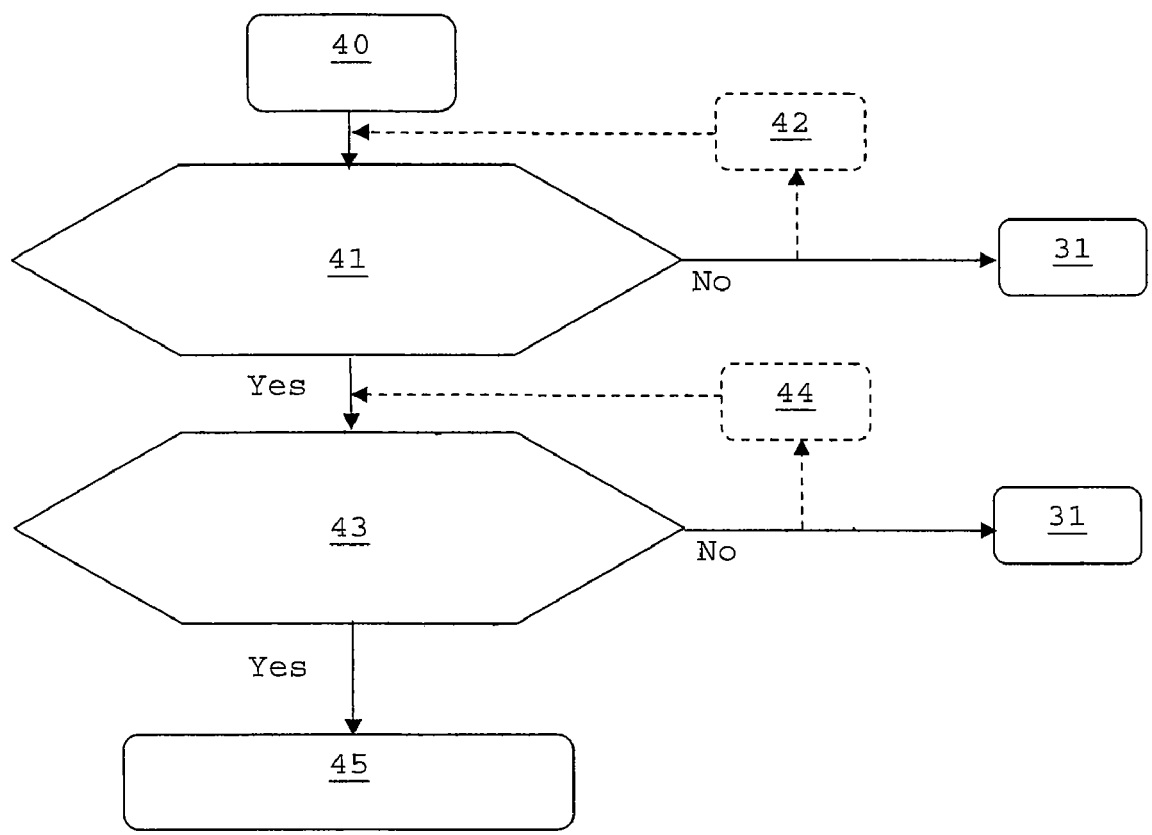
FIG. 14 is a flow chart of the currently most preferred embodiment of the method according to the invention.

FIG. 14 shows a flow chart of the most preferred embodiment of the method according to the invention. In a first step 40 the method depicted in FIG. 13 is performed. After a valid set of states has been assigned to the stitches of the allocated fabric part a double control is started including steps 41 and 43. In step 41 the number of stitches having the state "on" and the number of stitches having the state "off" is evaluated for each row of the allocated part of the fabric. Then it is checked if the number of stitches having the same state lies between 2 and 6, including the values 2 and 6. If this criteria is not fulfilled, then the method is preferably restarted by going back to step 31 (confer FIG. 13) and randomly assigning a state to each stitch of the allocated part of the fabric. Alternatively or additionally the states "on" and "off" can be randomly assigned anew to each of the stitches of the considered row in step 42 if the determined number of stitches having the same state is greater than 6 or smaller than 2. After this, step 42 is performed again.

In step 43 the number of stitches having the state "on" and the number of stitches having the state "off" is evaluated for each column of the allocated part of the fabric. Then it is checked, if the number of stitches having the same state lies between 2 and 20, including the values 2 and 20. If this is not the case, the method is preferably restarted at step 31 (confirm FIG. 13) by randomly assigning a state to each stitch. Alternatively or additionally the states "on" and "off" may be randomly assigned anew to each stitch of the considered in step 44. After this, step 43 is performed again.

The steps 41 and 43 may be performed in different ordering. That is, step 43 may be performed before the step 41. After the criteria of the steps 41 and 43 are fulfilled a valid, double-checked set of states for the stitches of the allocated fabric part is obtained and the method can be finished in step 45.

Figure 15:
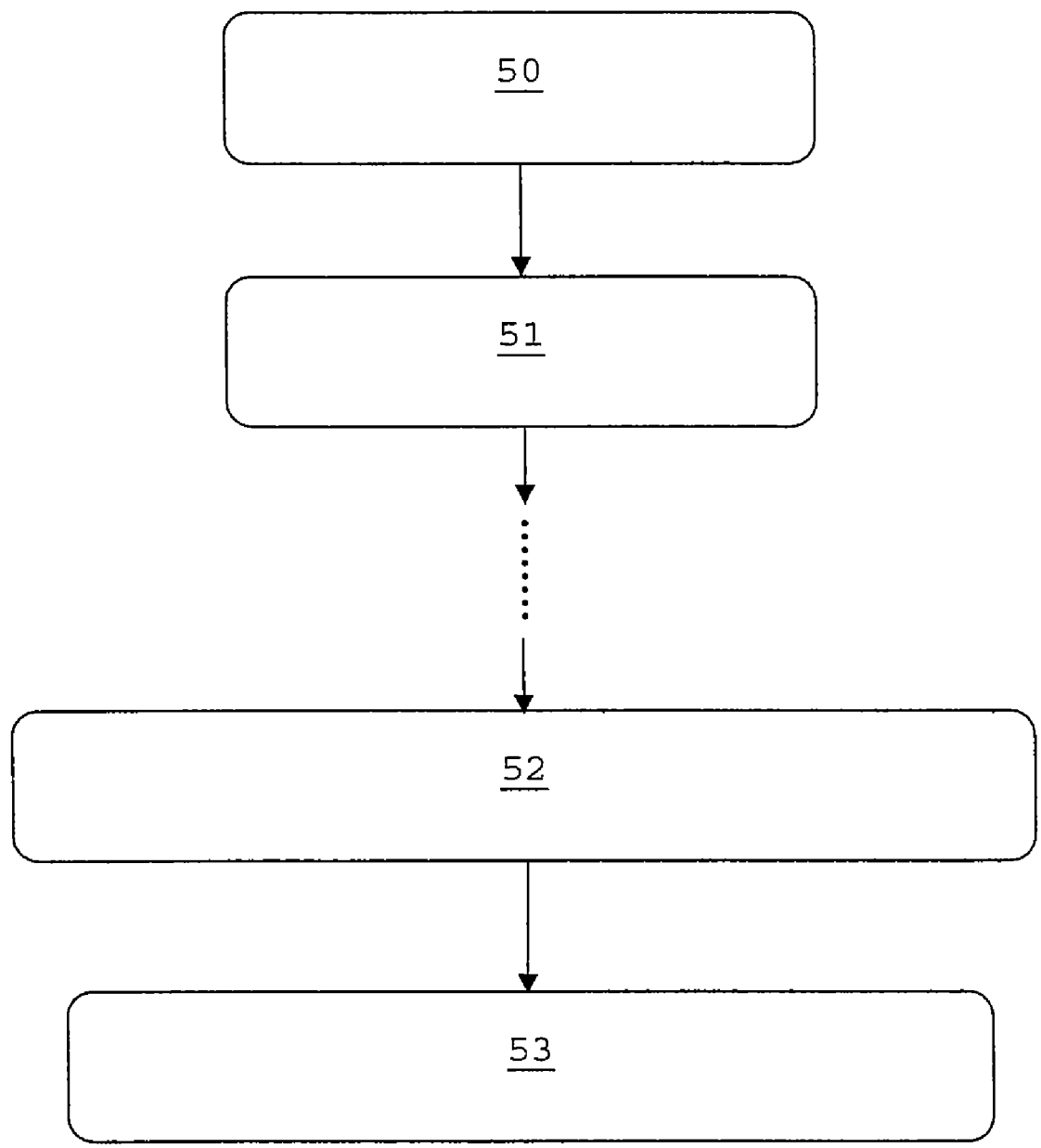
FIG. 15 is a flow chart of a further preferred embodiment of the method according to the invention.

FIG. 15 displays a further preferred embodiment of the method according to the invention. After the method depicted in FIG. 14 (or alternatively the method depicted in FIG. 13) has been performed in step 50, leading to the assignment of a valid set of states to the stitches of a first allocated part of a fabric then the method depicted in FIG. 14 (or alternatively the method depicted in FIG. 13) can be performed on the next part of the fabric, preferably involving the same number of rows and columns, in step 51. In this manner the method my be applied to all parts of the fabric having preferably the same number of rows and columns until the entire fabric or the entire medical compression garment, respectively, consists of stitches to which valid states according to the method of the invention have been assigned. Steps 52 and 53 represent the assignment of states to the stitches of the penultimate and the final part of the fabric.

Just using the stitch pattern of the first allocated part for consecutive parts of the fabric will not lead to the same random or fuzzy appearance of the entire fabric or medical compression stocking, respectively, but to an overall repetitive stitch pattern.

Figure 16:
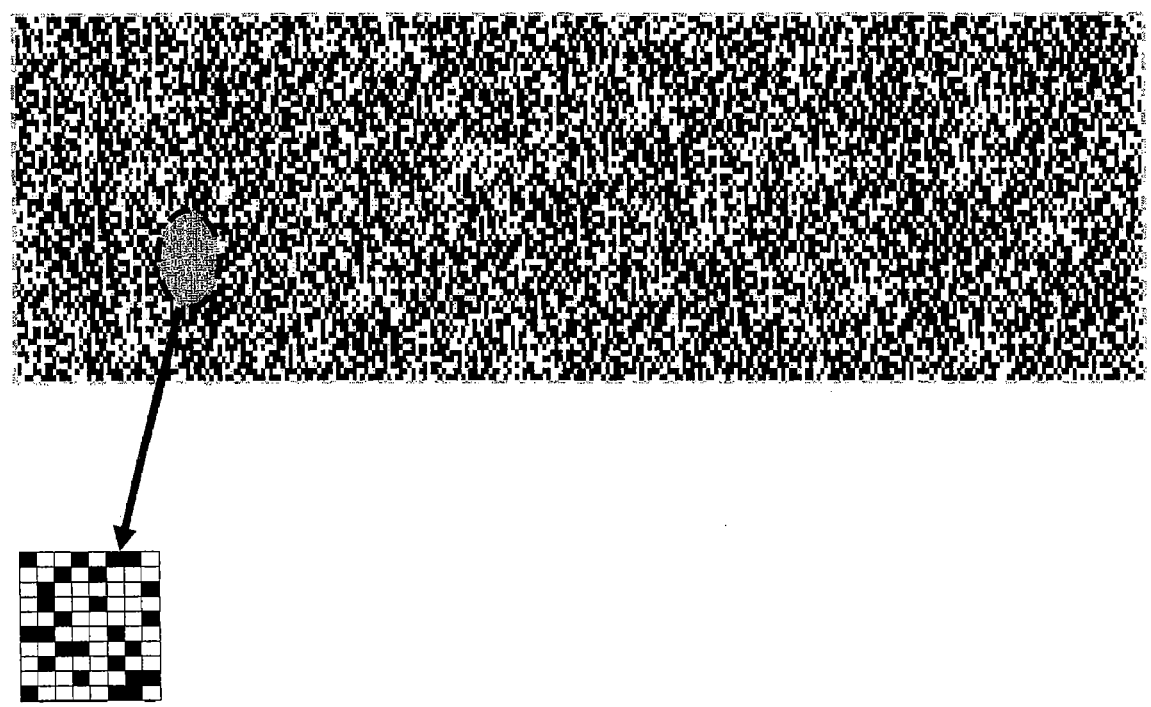
FIGS. 16 to 20 show examples of diagrams illustrating the states of stitches of stitch patterns generated by the method according to the invention.
Figure 17:
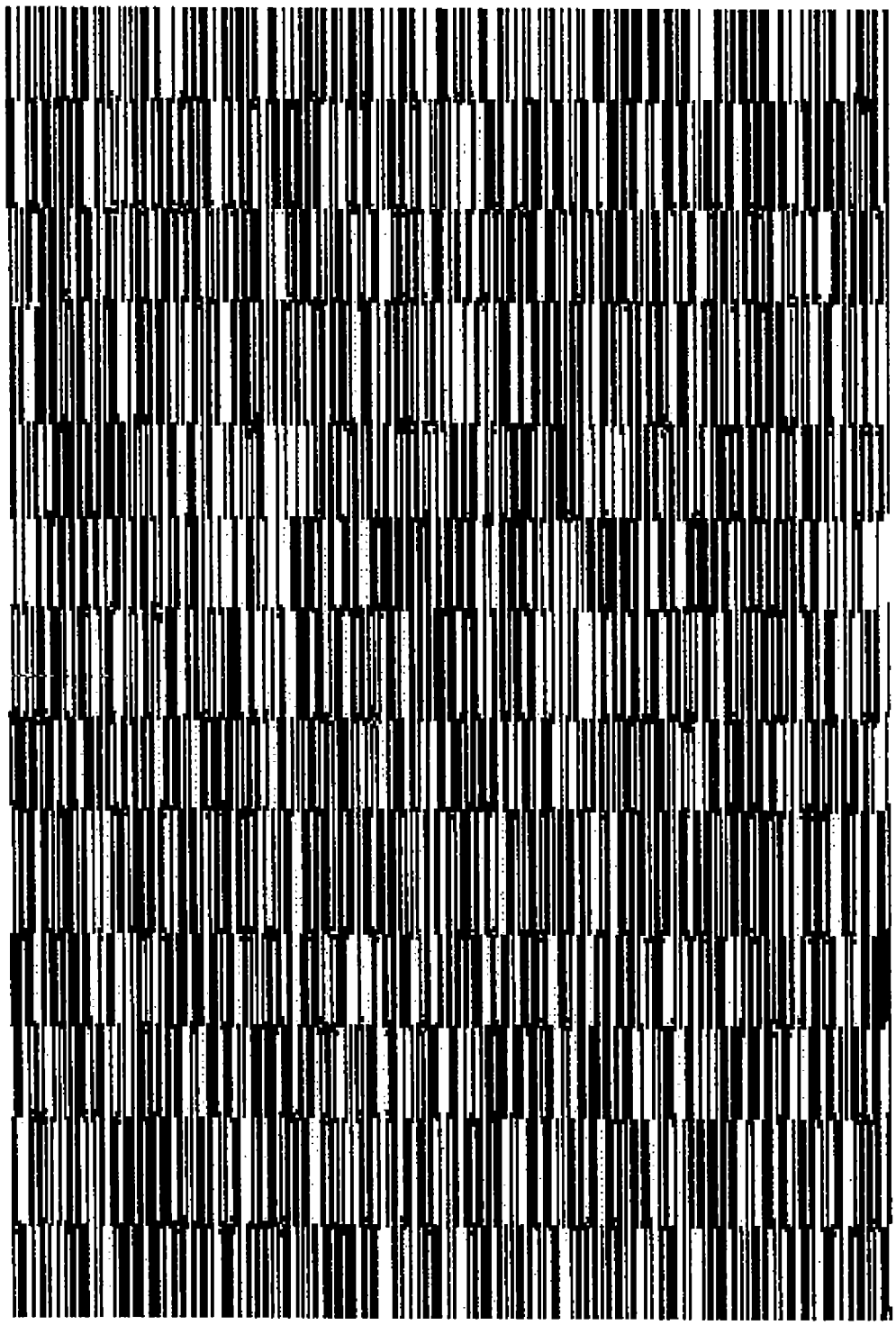
Figure 18:
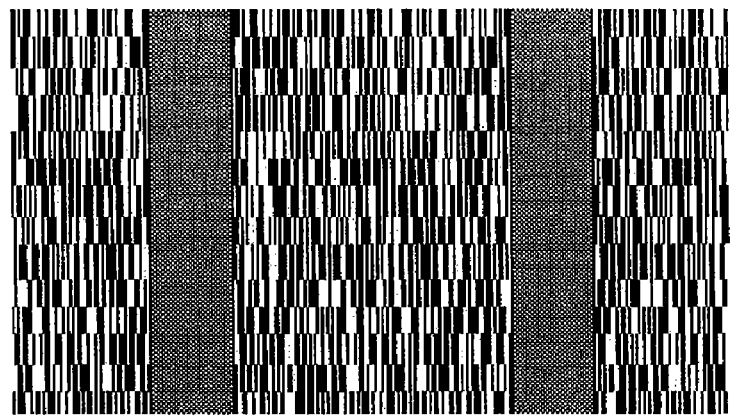
Figure 19:
Figure 20:
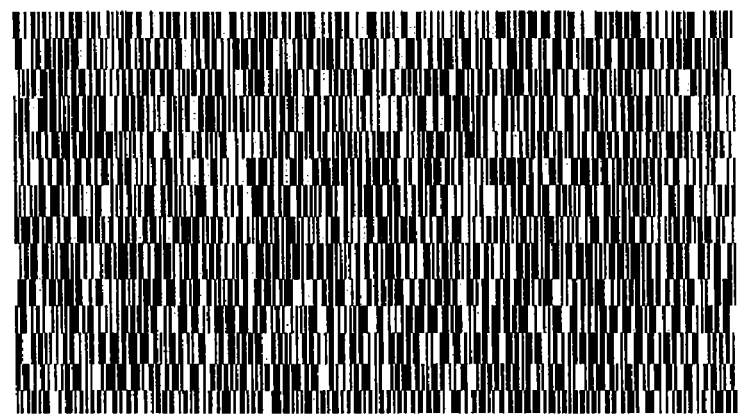

In FIGS. 16 to 18 further examples of diagrams are shown that illustrate the states of stitches of stitch patterns generated by the method according to the invention. The fuzzy stitch zones, i.e. the zones having a random or fuzzy appearance, may also be alternated with other repetitive patterns, e.g. the rib 1/3 stitch pattern and/or the plain stitch pattern (confer FIG. 18).

It is to be understood that while certain embodiments of the present invention have been illustrated and described herein, it is not to be limited to the specific embodiments described and shown.

The invention claimed is:

1. A method for assigning states to stitches of a fabric, wherein a state is one of a first state and a second state and the stitches are formed with an inlaid yarn and a loop yarn and in said first state of a stitch the loop yarn is positioned in front of the inlaid yarn and in said second state of a stitch the loop yarn is positioned behind the inlaid yarn, said method comprising steps of:
   a) allocating a part of the fabric,
   b) randomly assigning a state to each stitch of the allocated part of the fabric,
   c) evaluating the ratio between the number of stitches in the first state and the number of stitches in the second state,
   d) checking if the ratio lies within a predefined range of values, and
   e) restarting at step b) if the ratio lies outside of the predefined range.

2. The method of claim 1, wherein least value of the predefined range is 0.2 and the greatest value of the predefined range is 0.8.

3. The method of claim 1, further comprising the following steps:
   f) evaluating the number of stitches in the first state and the number of stitches in the second state for each row of the allocated part of the fabric,
   g) checking if the number of stitches in the same state lies between 2 and 6, and
   h) restarting at step b) if the number of stitches in the same state is greater than 6 or smaller than 2.

4. The method of claim 3, further comprising steps:
   i) evaluating the number of stitches in the first state and the number of stitches in the second state for each column of the allocated part of the fabric,
   j) checking if the number of stitches in the same state lies between 2 and 20, and
   k) restarting at step b) if the number of stitches in the same state is greater than 20 or smaller than 2.

5. The method of claim 1, wherein after a valid state has been assigned to each stitch of the allocated part of the fabric a further part of the fabric is allocated and the method steps are performed on said further part of the fabric.

6. The method of claim 1, with the method being performed on stitches of a fabric made by a knitting machine with 630 to 1260 needles per meter.

7. The method of claim 1, wherein the inlaid yarn comprises an elastic material with a yarn count of 200 dtex to 1500 dtex.

8. The method of claim 7, wherein the inlaid yarn is covered by a first covering yarn with a yarn count of 22 dtex to 400 dtex.

9. The method of claim 8, wherein the loop yarn comprises elastic material with a yarn count of 11 dtex to 78 dtex.

10. The method of claim 9, wherein the loop yarn is covered by a second covering yarn with a yarn count of 22 dtex to 200 dtex.

11. The method of claim 2, further comprising the following steps:
   f) evaluating the number of stitches in the first state and the number of stitches in the second state for each row of the allocated part of the fabric,
   g) checking if the number of stitches in the same state lies between 2 and 6, and
   h) restarting at step b) if the number of stitches in the same state is greater than 6 or smaller than 2.

12. The method of claim 1, further comprising the following steps:
   f) evaluating the number of stitches in the first state and the number of stitches in the second state for each column of the allocated part of the fabric,
   g) checking if the number of stitches in the same state lies between 2 and 20, and
   h) restarting at step b) if the number of stitches in the same state is greater than 20 or smaller than 2.

13. The method of claim 1, wherein the inlaid yarn is covered by a first covering yarn and the loop yarn is covered by a second covering yarn.

14. The method of claim 13, wherein the inlaid yarn is dyed in a different shade of color than the loop yarn and/or the second covering yarn and the first covering yarn is dyed in a different shade of color than the loop yarn and/or the second covering yarn.

15. The method of claim 13, wherein the inlaid yarn is dyed in a different shade of color than the loop yarn and/or the second covering yarn.

16. The method of claim 13, wherein the first covering yarn is dyed in a different shade of color than the loop yarn and/or the second covering yarn.

* * * * *